United States Patent
Stark et al.

(10) Patent No.: US 11,224,602 B2
(45) Date of Patent: Jan. 18, 2022

(54) OCULAR INSERT COMPOSITION OF A SEMI-CRYSTALLINE OR CRYSTALLINE PHARMACEUTICALLY ACTIVE AGENT

(71) Applicant: ForSight Visions, Inc., Parsippany, NJ (US)

(72) Inventors: Logan Stark, Parsippany, NJ (US); Rachna Jain, Parsippany, NJ (US); Ravi Srinivasan, Parsippany, NJ (US); Cary J. Reich, Parsippany, NJ (US); Carlos Schuler, Parsippany, NJ (US)

(73) Assignee: ForSight Vision5, Inc., North Chicago, IL (US)

( * ) Notice: Subject to any disclaimer, the term of this patent is extended or adjusted under 35 U.S.C. 154(b) by 0 days.

(21) Appl. No.: 16/243,842

(22) Filed: Jan. 9, 2019

(65) Prior Publication Data

US 2019/0142842 A1    May 16, 2019

Related U.S. Application Data

(63) Continuation of application No. 15/096,329, filed on Apr. 12, 2016, now abandoned.

(60) Provisional application No. 62/146,702, filed on Apr. 13, 2015.

(51) Int. Cl.
*A61K 31/5575* (2006.01)
*A61K 9/00* (2006.01)
*A61K 47/34* (2017.01)

(52) U.S. Cl.
CPC ........ *A61K 31/5575* (2013.01); *A61K 9/0051* (2013.01); *A61K 47/34* (2013.01)

(58) Field of Classification Search
CPC .................................................. A61K 31/5575
See application file for complete search history.

(56) References Cited

U.S. PATENT DOCUMENTS

| | | |
|---|---|---|
| 3,113,076 A | 12/1963 | Jacobs |
| 3,312,215 A | 4/1967 | Silber et al. |
| 3,416,530 A | 12/1968 | Ness |
| 3,545,439 A | 12/1970 | Kalamazoo et al. |
| 3,566,874 A | 3/1971 | Shepherd et al. |
| 3,618,604 A | 11/1971 | Ness |
| 3,626,940 A | 12/1971 | Zaffaroni |
| 3,710,796 A | 1/1973 | Neefe |
| 3,760,805 A | 9/1973 | Higuchi |
| 3,811,444 A | 5/1974 | Heller et al. |
| 3,826,258 A | 7/1974 | Abraham |
| 3,828,777 A | 8/1974 | Ness |
| 3,845,201 A | 10/1974 | Haddad et al. |
| 3,867,519 A | 2/1975 | Michaels |
| 3,903,880 A | 9/1975 | Higuchi et al. |
| 3,916,899 A | 11/1975 | Theeuwes et al. |
| 3,920,805 A | 11/1975 | Roseman |
| 3,926,188 A | 12/1975 | Baker et al. |
| 3,960,150 A | 6/1976 | Hussain et al. |
| 3,961,628 A | 6/1976 | Arnold |
| 3,962,414 A | 6/1976 | Michaels |
| 3,963,025 A | 6/1976 | Whitaker et al. |
| 3,991,760 A | 11/1976 | Drobish et al. |
| 3,993,073 A | 11/1976 | Zaffaroni |
| 3,995,633 A | 12/1976 | Gougeon |
| 3,995,634 A | 12/1976 | Drobish |
| 3,995,635 A | 12/1976 | Higuchi et al. |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,335 A | 3/1977 | Arnold |
| 4,016,251 A | 4/1977 | Higuchi et al. |
| 4,052,505 A | 10/1977 | Higuchi et al. |
| 4,057,619 A | 11/1977 | Higuchi et al. |
| 4,067,961 A | 1/1978 | Laughlin |
| 4,093,709 A | 6/1978 | Choi et al. |
| 4,131,648 A | 12/1978 | Choi et al. |
| 4,155,991 A | 5/1979 | Schopflin et al. |
| 4,157,864 A | 6/1979 | Koller et al. |
| 4,160,452 A | 7/1979 | Theeuwes |
| 4,164,560 A | 8/1979 | Folkman et al. |
| 4,177,256 A | 12/1979 | Michaels et al. |
| 4,179,497 A | 12/1979 | Cohen et al. |
| 4,190,642 A | 2/1980 | Gale et al. |
| 4,201,210 A | 5/1980 | Hughes et al. |

(Continued)

FOREIGN PATENT DOCUMENTS

| | | |
|---|---|---|
| AU | 2013213742 A1 | 8/2013 |
| CN | 1630494 A | 6/2005 |

(Continued)

OTHER PUBLICATIONS

Lumigan (Year: 2006).*
Antisensor. PEEK Chemicoal Compatibility & Resistanace Chart. (Year: 2015).*
Mahomed et al. Swelling of Medical Grade Silicones in Liquids and Calculation of Their Cross-link Densities. (Year: 2009).*
Behrens et al. (2006) "Dysfunctional Tear Syndrome. A Delphi Approach to Treatment Recommendations." *Cornea* vol. 25, No. 7, pp. 900-907.

(Continued)

*Primary Examiner* — Sarah Alawadi
(74) *Attorney, Agent, or Firm* — Mintz, Levin, Cohn, Ferris, Glovsky and Popeo, P.C.

(57) ABSTRACT

The present disclosure includes compositions of a semi-crystalline or crystalline pharmaceutically active agent dispersed in a polymer matrix, in which the active agent is less degraded and, therefore, has lower level of impurities. The present disclosure further includes a method of reducing or preventing physical and chemical degradation of a semi-crystalline or crystalline active agent pharmaceutically active agent dispersed in a polymer matrix. A method of preparation of the composition is also included in this disclosure.

10 Claims, 5 Drawing Sheets

(56) References Cited

U.S. PATENT DOCUMENTS

| | | |
|---|---|---|
| 4,215,691 A | 8/1980 | Wong |
| 4,237,885 A | 12/1980 | Wong et al. |
| 4,249,531 A | 2/1981 | Heller et al. |
| 4,281,654 A | 8/1981 | Shell et al. |
| 4,285,987 A | 8/1981 | Ayer et al. |
| 4,292,965 A | 10/1981 | Nash et al. |
| 4,303,637 A | 12/1981 | Shell et al. |
| 4,304,765 A | 12/1981 | Shell et al. |
| 4,322,323 A | 3/1982 | Capozza |
| 4,343,787 A | 8/1982 | Katz |
| 4,432,964 A | 2/1984 | Shell et al. |
| 4,439,198 A | 3/1984 | Brightman, II et al. |
| 4,452,776 A | 6/1984 | Refojo |
| 4,469,671 A | 9/1984 | Zimmerman et al. |
| 4,484,922 A | 11/1984 | Rosenwald |
| 4,524,776 A | 6/1985 | Withers et al. |
| 4,540,417 A | 9/1985 | Poler |
| 4,652,099 A | 3/1987 | Lichtman |
| 4,678,466 A | 7/1987 | Rosenwald |
| 4,822,616 A | 4/1989 | Zimmermann et al. |
| 4,888,074 A | 12/1989 | Pocknell |
| 4,961,931 A | 10/1990 | Wong |
| 4,973,304 A | 11/1990 | Graham et al. |
| 5,071,657 A | 12/1991 | Oloff et al. |
| 5,098,443 A | 3/1992 | Parel et al. |
| 5,137,728 A | 8/1992 | Bawa |
| 5,147,647 A | 9/1992 | Darougar |
| 5,178,635 A | 1/1993 | Gwon et al. |
| 5,205,611 A | 4/1993 | Stephens |
| 5,248,700 A | 9/1993 | Lance |
| 5,300,114 A | 4/1994 | Gwon et al. |
| 5,314,419 A | 5/1994 | Felling |
| 5,322,691 A | 6/1994 | Darougar et al. |
| 5,370,607 A | 12/1994 | Memmen |
| 5,378,475 A | 1/1995 | Smith et al. |
| 5,395,618 A | 3/1995 | Darougar et al. |
| 5,443,505 A | 8/1995 | Wong et al. |
| 5,472,436 A | 12/1995 | Fremstad |
| 5,474,780 A | 12/1995 | Chang |
| 5,476,511 A | 12/1995 | Gwon et al. |
| 5,496,811 A | 3/1996 | Aviv et al. |
| 5,605,696 A | 2/1997 | Eury et al. |
| 5,607,978 A | 3/1997 | Woodward et al. |
| 5,618,274 A | 4/1997 | Rosenthal |
| 5,688,819 A | 11/1997 | Woodward et al. |
| 5,694,947 A | 12/1997 | Lehtinen et al. |
| 5,773,019 A | 6/1998 | Ashton et al. |
| 5,773,021 A | 6/1998 | Gurtler et al. |
| 5,788,977 A | 8/1998 | Aguadisch et al. |
| 5,824,086 A | 10/1998 | Silvestrini |
| 5,851,547 A | 12/1998 | Fujioka et al. |
| 5,855,906 A | 1/1999 | McClay |
| 5,902,598 A | 5/1999 | Chen et al. |
| 5,972,372 A | 10/1999 | Saleh et al. |
| 5,989,579 A | 11/1999 | Darougar et al. |
| 5,989,581 A | 11/1999 | Groenewegen |
| 6,001,386 A | 12/1999 | Ashton et al. |
| 6,015,213 A | 1/2000 | Nakada et al. |
| 6,096,076 A | 8/2000 | Silvestrini |
| 6,109,537 A | 8/2000 | Heath |
| 6,120,460 A | 9/2000 | Abreu |
| 6,146,366 A | 11/2000 | Schachar |
| 6,149,685 A | 11/2000 | Sigoloff |
| 6,217,896 B1 | 4/2001 | Benjamin |
| 6,264,971 B1 | 7/2001 | Darougar et al. |
| 6,361,780 B1 | 3/2002 | Ley et al. |
| 6,375,642 B1 | 4/2002 | Grieshaber et al. |
| 6,375,972 B1 | 4/2002 | Guo et al. |
| 6,394,094 B1 | 5/2002 | McKenna et al. |
| 6,403,649 B1 | 6/2002 | Woodward et al. |
| 6,485,735 B1 | 11/2002 | Steen et al. |
| 6,547,714 B1 | 4/2003 | Dailey |
| 6,634,576 B2 | 10/2003 | Verhoff et al. |
| 6,669,950 B2 | 12/2003 | Yaacobi |
| 6,719,750 B2 | 4/2004 | Varner et al. |
| 6,746,686 B2 | 6/2004 | Hughes et al. |
| 6,841,574 B2 | 1/2005 | Mo et al. |
| 6,939,569 B1 | 9/2005 | Green et al. |
| 6,964,781 B2 | 11/2005 | Brubaker |
| 6,966,927 B1 | 11/2005 | Silverstrini |
| 6,986,900 B2 | 1/2006 | Yaacobi |
| 6,991,808 B2 | 1/2006 | Brubaker et al. |
| 7,017,580 B2 | 3/2006 | Prescott et al. |
| 7,094,226 B2 | 8/2006 | Yaacobi |
| 7,157,590 B2 | 1/2007 | Gutman et al. |
| 7,166,730 B2 | 1/2007 | Gutman et al. |
| 7,195,774 B2 | 3/2007 | Carvalho et al. |
| 7,488,343 B2 | 2/2009 | O'Brien et al. |
| 7,544,371 B2 | 6/2009 | Kunzler et al. |
| 7,611,886 B2 | 11/2009 | Effenberger et al. |
| 7,762,662 B1 | 7/2010 | Eno |
| 7,785,578 B2 | 8/2010 | Miller et al. |
| 7,799,336 B2 | 9/2010 | Hughes |
| 7,833,545 B2 | 11/2010 | Ron et al. |
| 7,851,504 B2 | 12/2010 | Chang et al. |
| 7,862,552 B2 | 1/2011 | McIntyre et al. |
| 7,910,126 B2 | 3/2011 | Ahmed et al. |
| 7,947,740 B2 | 5/2011 | Gutman et al. |
| 7,985,208 B2 | 7/2011 | Christensen |
| 7,993,634 B2 * | 8/2011 | Hughes ............... A61K 9/0051 424/78.04 |
| 7,998,497 B2 | 8/2011 | de Juan, Jr. et al. |
| 8,017,655 B2 | 9/2011 | Woodward et al. |
| 8,021,680 B2 | 9/2011 | Anderson et al. |
| 8,034,105 B2 | 10/2011 | Stegmann et al. |
| 8,278,353 B2 | 10/2012 | Chang et al. |
| 8,299,118 B2 | 10/2012 | Chang et al. |
| 8,309,605 B2 | 11/2012 | Chang et al. |
| 8,338,479 B2 | 12/2012 | Chang et al. |
| 8,469,934 B2 | 6/2013 | Weiner et al. |
| 8,524,777 B2 | 9/2013 | Chang et al. |
| 8,629,185 B2 | 1/2014 | Ambrus et al. |
| 8,663,194 B2 | 3/2014 | Ambati et al. |
| 8,664,275 B2 | 3/2014 | He et al. |
| 8,715,712 B2 | 5/2014 | de Juan, Jr. et al. |
| 9,486,362 B2 | 11/2016 | Shikamura et al. |
| 9,907,694 B2 | 3/2018 | Clarke et al. |
| 9,937,335 B2 | 4/2018 | Moss et al. |
| 9,999,595 B2 | 6/2018 | Rakic et al. |
| 10,004,636 B2 | 6/2018 | Alster et al. |
| 2002/0026176 A1 | 2/2002 | Varner et al. |
| 2002/0047058 A1 | 4/2002 | Verhoff et al. |
| 2002/0115985 A1 | 8/2002 | Larson et al. |
| 2003/0088307 A1 | 5/2003 | Shulze et al. |
| 2003/0149479 A1 | 8/2003 | Snyder et al. |
| 2003/0176854 A1 | 9/2003 | Rodstrom |
| 2004/0042073 A1 | 3/2004 | Pynson |
| 2004/0115234 A1 | 6/2004 | Gewirtz |
| 2004/0116593 A1 * | 6/2004 | Lai .................. G02B 1/043 524/588 |
| 2004/0121014 A1 | 6/2004 | Guo et al. |
| 2004/0133155 A1 | 7/2004 | Varner et al. |
| 2004/0170685 A1 | 9/2004 | Carpenter et al. |
| 2004/0220660 A1 | 11/2004 | Shanley et al. |
| 2004/0241243 A1 | 12/2004 | Lin et al. |
| 2004/0249364 A1 | 12/2004 | Kaploun |
| 2004/0265355 A1 | 12/2004 | Shalaby |
| 2005/0019371 A1 | 1/2005 | Anderson et al. |
| 2005/0042292 A1 | 2/2005 | Muldoon et al. |
| 2005/0048099 A1 | 3/2005 | Shiah et al. |
| 2005/0053639 A1 | 3/2005 | Shalaby |
| 2005/0060021 A1 | 3/2005 | O'Brien et al. |
| 2005/0125059 A1 | 6/2005 | Pinchuk et al. |
| 2005/0163844 A1 | 7/2005 | Ashton |
| 2005/0196424 A1 | 9/2005 | Chappa |
| 2005/0197651 A1 | 9/2005 | Chen et al. |
| 2005/0228473 A1 | 10/2005 | Brown |
| 2005/0228482 A1 | 10/2005 | Herzog et al. |
| 2005/0232972 A1 | 10/2005 | Odrich |
| 2005/0244461 A1 | 11/2005 | Nivaggioli et al. |
| 2005/0244464 A1 | 11/2005 | Hughes |
| 2005/0276841 A1 | 12/2005 | Davis et al. |
| 2005/0288197 A1 | 12/2005 | Horn |
| 2006/0024350 A1 | 2/2006 | Varner et al. |

(56) References Cited

U.S. PATENT DOCUMENTS

| | | |
|---|---|---|
| 2006/0034891 A1 | 2/2006 | Lawin et al. |
| 2006/0140867 A1 | 6/2006 | Helfer et al. |
| 2006/0182781 A1 | 8/2006 | Hughes et al. |
| 2006/0185678 A1 | 8/2006 | Bronnenkant et al. |
| 2006/0212115 A1 | 9/2006 | Bas |
| 2006/0216328 A1 | 9/2006 | Kis et al. |
| 2006/0235513 A1 | 10/2006 | Price |
| 2006/0246112 A1 | 11/2006 | Snyder et al. |
| 2006/0264912 A1 | 11/2006 | McIntyre et al. |
| 2006/0292222 A1 | 12/2006 | Jonasse |
| 2007/0112318 A1 | 5/2007 | Leahy et al. |
| 2007/0134305 A1 | 6/2007 | Zilberman |
| 2007/0196433 A1 | 8/2007 | Ron et al. |
| 2007/0202150 A1 | 8/2007 | Dave |
| 2007/0212387 A1 | 9/2007 | Patravale et al. |
| 2007/0243230 A1 | 10/2007 | Juan et al. |
| 2007/0269487 A1 | 11/2007 | Juan et al. |
| 2008/0090911 A1 | 4/2008 | Frank et al. |
| 2008/0097591 A1 | 4/2008 | Savage et al. |
| 2008/0103584 A1 | 5/2008 | Su et al. |
| 2008/0145403 A1 | 6/2008 | Spada et al. |
| 2008/0145406 A1 | 6/2008 | Asgharian et al. |
| 2008/0181930 A1 | 7/2008 | Rodstrom et al. |
| 2008/0243095 A1 | 10/2008 | Kaiser et al. |
| 2009/0005864 A1 | 1/2009 | Eggleston |
| 2009/0012836 A1 | 1/2009 | Weissbach et al. |
| 2009/0081278 A1 | 3/2009 | Graaff et al. |
| 2009/0082863 A1 | 3/2009 | Schieber et al. |
| 2009/0092654 A1 | 4/2009 | Juan, Jr. et al. |
| 2009/0104243 A1 | 4/2009 | Utkhede et al. |
| 2009/0104248 A1 | 4/2009 | Rapacki et al. |
| 2009/0110756 A1 | 4/2009 | McCray, Jr. et al. |
| 2009/0143752 A1 | 6/2009 | Higuchi et al. |
| 2009/0148485 A1 | 6/2009 | Whitehead |
| 2009/0155326 A1 | 6/2009 | Mack et al. |
| 2009/0155338 A1 | 6/2009 | Conway et al. |
| 2009/0162417 A1 | 6/2009 | Eells |
| 2009/0163596 A1 | 6/2009 | Gutman et al. |
| 2009/0196903 A1 | 8/2009 | Kliman |
| 2009/0220573 A1 | 9/2009 | Kaufman |
| 2009/0234005 A1 | 9/2009 | Ishida et al. |
| 2009/0252807 A1 | 10/2009 | Jenkins et al. |
| 2009/0280158 A1 | 11/2009 | Butuner |
| 2009/0287300 A1 | 11/2009 | Dave et al. |
| 2009/0291120 A1 | 11/2009 | Tuominen et al. |
| 2009/0312724 A1 | 12/2009 | Pipkin et al. |
| 2009/0312836 A1 | 12/2009 | Pinchuk et al. |
| 2009/0318549 A1 | 12/2009 | Butuner |
| 2010/0040671 A1 | 2/2010 | Ahmed et al. |
| 2010/0055139 A1 | 3/2010 | Lee |
| 2010/0069857 A1 | 3/2010 | Christensen |
| 2010/0074942 A1 | 3/2010 | Ratner et al. |
| 2010/0114309 A1 | 5/2010 | de Juan, Jr. et al. |
| 2010/0124565 A1 | 5/2010 | Spada et al. |
| 2010/0140114 A1 | 6/2010 | Pruitt et al. |
| 2010/0166841 A1 | 7/2010 | Roth et al. |
| 2010/0178316 A1 | 7/2010 | Chauhan et al. |
| 2010/0209477 A1 | 8/2010 | Butuner et al. |
| 2010/0209478 A1 | 8/2010 | Sawhney et al. |
| 2010/0226962 A1 | 9/2010 | Rodstrom et al. |
| 2010/0233241 A1 | 9/2010 | Leahy et al. |
| 2010/0266664 A1 | 10/2010 | Asgharian et al. |
| 2010/0278898 A1 | 11/2010 | Hughes et al. |
| 2010/0331796 A1 | 12/2010 | Leahy et al. |
| 2011/0008421 A1 | 1/2011 | Hara et al. |
| 2011/0009958 A1 | 1/2011 | Wardle et al. |
| 2011/0105986 A1 | 5/2011 | Bronstein et al. |
| 2011/0178340 A1 | 7/2011 | de Souza et al. |
| 2011/0184358 A1 | 7/2011 | Weiner et al. |
| 2011/0195123 A1 | 8/2011 | Shemi |
| 2011/0268783 A1 | 11/2011 | Shalaby et al. |
| 2011/0280909 A1 | 11/2011 | Moazed |
| 2011/0282328 A1 | 11/2011 | Ambati et al. |
| 2011/0288179 A1 | 11/2011 | Gutman et al. |
| 2012/0022473 A1 | 1/2012 | Shikamura et al. |
| 2012/0089072 A1 | 4/2012 | Cunningham, Jr. |
| 2012/0109054 A1 | 5/2012 | Thompson et al. |
| 2012/0116505 A1 | 5/2012 | Shahinpoor et al. |
| 2012/0136322 A1 | 5/2012 | Alster et al. |
| 2012/0168422 A1 | 7/2012 | Boyd et al. |
| 2012/0177716 A1 | 7/2012 | Ho et al. |
| 2012/0187594 A1 | 7/2012 | Utkhede et al. |
| 2012/0215184 A1 | 8/2012 | Lim |
| 2012/0244088 A1 | 9/2012 | Saxena et al. |
| 2012/0245505 A1 | 9/2012 | Robinson et al. |
| 2012/0253459 A1 | 10/2012 | Reich et al. |
| 2012/0269893 A1 | 10/2012 | Lee |
| 2012/0270946 A1 | 10/2012 | He et al. |
| 2013/0017243 A1 | 1/2013 | Shi et al. |
| 2013/0062809 A1 | 3/2013 | Ellis et al. |
| 2013/0090612 A1 | 4/2013 | de Juan, Jr. et al. |
| 2013/0142858 A1 | 6/2013 | Kopczynski et al. |
| 2013/0144128 A1 | 6/2013 | de Juan, Jr. et al. |
| 2013/0156752 A1 | 6/2013 | Jarrett et al. |
| 2013/0156840 A1 | 6/2013 | Basinger et al. |
| 2013/0177615 A1 | 7/2013 | Lee |
| 2013/0209538 A1 | 8/2013 | Venkatraman et al. |
| 2013/0261569 A1 | 10/2013 | Weiner et al. |
| 2014/0113974 A1 | 4/2014 | Ambrus et al. |
| 2014/0121612 A1 | 5/2014 | Rubin et al. |
| 2014/0135716 A1 | 5/2014 | Clarke et al. |
| 2015/0057689 A1 | 2/2015 | Epstein et al. |
| 2015/0133878 A1 | 5/2015 | de Juan, Jr. et al. |
| 2016/0022695 A1 | 1/2016 | Reich et al. |
| 2016/0243291 A1 | 8/2016 | Reich et al. |
| 2016/0296532 A1 | 10/2016 | Stark et al. |
| 2018/0085254 A1 | 3/2018 | Rubin et al. |
| 2018/0092926 A1 | 4/2018 | Reich et al. |
| 2018/0177634 A1 | 6/2018 | de Juan, Jr. et al. |
| 2019/0105198 A1 | 4/2019 | Alster et al. |
| 2020/0038240 A1 | 2/2020 | de Juan, Jr. et al. |

FOREIGN PATENT DOCUMENTS

| | | |
|---|---|---|
| CN | 100339058 C | 9/2007 |
| CN | 201012180 Y | 1/2008 |
| CN | 102026599 A | 4/2011 |
| CN | 102368975 A | 3/2012 |
| EP | 0660716 A1 | 7/1995 |
| EP | 0825980 A1 | 3/1998 |
| EP | 1397347 A2 | 3/2004 |
| EP | 1473003 A2 | 11/2004 |
| EP | 1853719 A2 | 11/2007 |
| EP | 1694641 B1 | 4/2009 |
| EP | 2497766 A1 | 9/2012 |
| EP | 2504313 A1 | 10/2012 |
| GB | 1372944 | 11/1974 |
| GB | 1529143 A | 10/1978 |
| IL | 143477 A | 7/2009 |
| JP | S48-036993 | 5/1973 |
| JP | S5560452 | 5/1980 |
| JP | S629561 B2 | 2/1987 |
| JP | H07067910 A | 3/1995 |
| JP | 2007167358 | 7/2007 |
| JP | 2008523917 A | 7/2008 |
| JP | 2010513555 A | 4/2010 |
| JP | 2010-517630 A | 5/2010 |
| JP | 2010538696 A | 12/2010 |
| JP | 2011520805 A | 7/2011 |
| JP | 2011-153127 A | 8/2011 |
| JP | 2012512904 A | 6/2012 |
| JP | 2012-518469 A | 8/2012 |
| RU | 2357709 C1 | 6/2009 |
| RU | 2414199 C2 | 3/2011 |
| SU | 404474 A1 | 10/1973 |
| WO | WO-92/014450 A1 | 9/1992 |
| WO | WO-95/01764 A2 | 1/1995 |
| WO | WO-97/02015 A1 | 1/1997 |
| WO | WO-97/43984 A1 | 11/1997 |
| WO | WO-02/076426 A2 | 10/2002 |
| WO | WO-02/096868 A2 | 12/2002 |
| WO | WO-2005/020907 A3 | 3/2005 |
| WO | WO-2006/066103 A2 | 6/2006 |
| WO | WO-2007/083293 A1 | 7/2007 |

(56) References Cited

FOREIGN PATENT DOCUMENTS

| WO | WO-2008/094989 A2 | 8/2008 |
| WO | WO-2009/035562 A2 | 3/2009 |
| WO | WO-2009/107753 A1 | 9/2009 |
| WO | WO-2009/140345 A2 | 11/2009 |
| WO | WO-2009/153206 A2 | 12/2009 |
| WO | WO-2010/096315 A1 | 8/2010 |
| WO | WO-2010/141729 | 12/2010 |
| WO | WO-2011/073134 A1 | 6/2011 |
| WO | WO-2012/011128 A1 | 1/2012 |
| WO | WO-2012/164324 A1 | 12/2012 |
| WO | WO-2013/040426 A2 | 3/2013 |
| WO | WO2014/160828 * | 10/2014 |
| WO | WO-2014/160828 A1 | 10/2014 |

OTHER PUBLICATIONS

Butrus et al. (2000) "Comparison of the Clinical Efficacy and Comfort of Olopatadine Hydrochloride 0.1% Ophthalmic Solution and Nedocromil Sodium 2% Ophthalmic Solution in the Human Conjunctival Allergen Challenge Model." *Clin. Ther.*, 22(12):1462-72.

Francis, I.C. (1984) "The Disposable Modified Fornix Flap for Cataract Surgery." *Aust. J. Ophthalmol.* 12:57-59.

Johnson et al. (2007) "Measurement of Ocular Surface Irritation on a Linear Interval Scale with the Ocular Comfort Index." *Invest. Ophthalmol. Vis. Sci.*, 48(10):4451-8.

Kawakita et al. "Measurement of fornix depth and area: a novel method of determining the severity of fornix shortening", Eye (2009) 23, 1115-1119.

Koch Eye Associates. Dry Eye. 1, 2012. [Retrieved on Nov. 12, 2014]. ; Retrieved from the Internet. <URL: http://kocheye.com/dry_eye.htm>. (1 page).

Kumari A. et al. "Ocular inserts—Advancement in therapy of eye diseases." J. Adv. Pharm. Technol. Res. Jun.-Sep. 2010, 1(3): 291-296. Web. Downloaded from Internet Jan. 4, 2018.

Polymer Systems Technology Limited. Material Safety Data Sheet MED-4800-7. 1-6, 2012. [Retrieved on Nov. 12, 2014]. Retrieved from the Internet. <URL: https://www.silicone-polymers.co.uk/pdfMaster/MED48007.pdf>.

Qi, et al. (2003) "Durometer Hardness and the Stress-Strain Behavior of Elastomeric Materials." *Rubber Chemistry and Technology*, 76(2):419-435.

Zeus Technical Newsletter. "Strength and Stiffness of Plastics". (Obtained from http://www.zeusinc.com/UserFiles/zeusinc/Documents/technical_newsletters/Zeus_StrengthStiffnessPlastics.pdf on Oct. 18, 2013). 11 pages.

* cited by examiner

OCULAR INSERT COMPOSITION OF A SEMI-CRYSTALLINE OR CRYSTALLINE PHARMACEUTICALLY ACTIVE AGENT

RELATED APPLICATIONS

This application is a continuation of U.S. patent application Ser. No. 15/096,329, filed Apr. 12, 2016, which claims priority to, and the benefit of, U.S. Provisional Application No. 62/146,702, filed on Apr. 13, 2015. The disclosures of the applications are hereby incorporated herein by reference in their entirety for all purposes.

BACKGROUND OF THE DISCLOSURE

Release rate of a pharmaceutically active agent from a delivery device, for example ocular insert, in which the active agent is dispersed in a polymer matrix, can have a high day 1 burst of the agent. This burst rate or the initial release rate compromises the efficacy of the device because prolonged delivery of the agent is undermined. In addition, chemical degradation of the active agent limits the duration the preparation can be stored and used. The present disclosure addresses these needs.

BRIEF SUMMARY OF THE DISCLOSURE

The present disclosure provides, inter alia, compositions of semi-crystalline or crystalline pharmaceutically active agents and a polymer. In aspects of this disclosure, the polymer forms a matrix, and the semi-crystalline or crystalline pharmaceutically active agents ("active agent(s)") are dispersed in the polymer matrix. In aspects of this disclosure, the compositions are an ocular composition. In embodiments, the active agent is bimatoprost.

The present disclosure provides, inter alia, a method of reducing or preventing degradation of a semi-crystalline or crystalline pharmaceutically active agent dispersed in a polymer matrix in an ocular insert composition, the method including washing the insert with an organic solvent. In embodiments, the ocular insert of the present disclosure is washed before it is sterilized during preparation of the composition.

The present disclosure provides, inter alia, a method of increasing stability of a semi-crystalline or crystalline pharmaceutically active agent dispersed in a polymer matrix in an ocular insert composition, the method including washing the insert with an organic solvent. In embodiments, the ocular insert of the present disclosure is washed before it is sterilized during preparation of the composition.

The present disclosure provides, inter alia, a method of preparing an ocular insert composition including a semi-crystalline or crystalline pharmaceutically active agent, e.g., bimatoprost, dispersed in a polymer matrix, the method including: mixing the active agent with a polymer; curing the polymer including the active agent; cooling the cured polymer including the active agent; washing the composition with an organic solvent, e.g., acetonitrile; and sterilizing the composition.

The present disclosure provides, inter alia, kits including an ocular insert in which a semi-crystalline or crystalline pharmaceutically active agent, e.g., bimatoprost, is dispersed in a polymer matrix.

The present disclosure provides, inter alia, a device having a ring shape which may be placed on or in an eye of a subject in need thereof to treat an ocular disease or disorder. For example, the ring shaped ocular insert of the present disclosure may be used to reduce intraocular pressure and/or treat glaucoma.

Embodiments of the present disclosure provides an ocular composition including a polymer matrix in which a semi-crystalline or crystalline pharmaceutically active agent is dispersed. For example, in embodiments, the pharmaceutically active agent is bimatoprost. In embodiments, the composition includes about 2% or less impurities. For example, in embodiments, the impurity in the composition is 15-keto bimatoprost. In embodiments, the composition includes about 1% or less 15-keto bimatoprost. In embodiments, the composition includes about 1% 15-keto bimatoprost. In embodiments, the composition includes less than about 1% 15-keto bimatoprost. In embodiments, the impurities include 5-trans bimatoprost. For example, in embodiments, the composition includes about 0.1% to about 1% 5-trans bimatoprost. In embodiments, the composition includes about 0.1% 5-trans bimatoprost and about 1% 15-keto bimatoprost. In embodiments, the composition includes about 0.2% 5-trans bimatoprost and about 1% 15-keto bimatoprost. In embodiments, the semi-crystalline or crystalline bimatoprost is chemically stable in the composition for 760 days. In embodiments, the matrix includes a thermosetting polymer or a thermoplastic polymer. In embodiments, the thermosetting polymer is silicone. In embodiments, the silicone included in the composition is liquid silicone rubber, e.g., MED-4810, MED-4820, MED-4830, MED-4840, MED-4842, MED1-4855, MED-4860, MED-4870, MED-4880, or equivalents thereof. In embodiments, the composition is configured as an ocular insert. In embodiments, the ocular insert is a ring shaped ocular insert. In embodiments, the ocular ring insert of the present disclosure has a diameter of about 10 mm to about 40 mm and a cross-sectional thickness of about 0.1 mm to about 1.5 mm. For example, ocular ring insert of the present disclosure has a diameter of about 20 mm to about 30 mm and the cross-sectional thickness is about 0.5 mm to about 1.5 mm. In embodiments, the active agent is about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, or about 22% by weight of the composition. In embodiments, the active agent is bimatoprost.

In embodiments, the present disclosure provides a method of reducing or preventing degradation of a semi-crystalline or crystalline pharmaceutically active agent dispersed in a polymer matrix in an ocular insert composition, the method including washing the insert with an organic solvent. In embodiments, the method includes washing the insert before sterilizing the composition. In embodiments, the method reduces or prevents degradation of a semi-crystalline or crystalline form of the active agent bimatoprost dispersed in a polymer matrix in an ocular insert composition. For example, in embodiments, the method reduces or prevents degradation of the bimatoprost to 5-trans bimatoprost and/or 15-keto bimatoprost. In embodiments, equal to or less than about 1% 15-keto bimatoprost is formed by the method. In embodiments, the method includes washing the insert with an organic solvent, e.g., acetonitrile. In embodiments, the method includes washing the insert with acetonitrile for less than 48 hours. For example, in embodiments, the method includes washing the insert with acetonitrile for equal to or less than 8 hours. For example, in embodiments, the method includes washing the insert with acetonitrile for equal to or less than 6 hours. For example, in embodiments, the method includes washing the insert with acetonitrile for equal to or less than 4 hours. In embodiments, the method includes washing the insert at less than about 60° C. In embodiments, the method includes washing the insert at about room temperature. In embodiments, the method includes reducing or preventing degradation of a semi-crystalline or crystalline pharmaceutically active agent dispersed in a polymer matrix, which includes a thermosetting polymer or a thermoplastic polymer. In embodiments, the thermosetting polymer is silicone. In embodiments, the silicone is liquid silicone rubber, e.g., MED-4810, MED-4820, MED-4830, MED-4840, MED-4842, MED1-4855, MED-4860, MED-4870, MED-4880, or equivalents thereof. In embodiments, the ocular insert is a ring shaped ocular insert. In embodiments, the method provides that after the method is performed the active agent in the polymer matrix is chemically stable in the semi-crystalline or crystalline form for 760 days. In embodiments, the method provides that after the method is performed the active agent in the polymer matrix is chemically stable in the semi-crystalline or crystalline form for 18 months, 12 months, 6 months, or 3 months.

In embodiments, the present disclosure provides a method of preparing an ocular insert composition comprising a semi-crystalline or crystalline pharmaceutically active agent dispersed in a polymer matrix, the method including: mixing the active agent with a polymer; curing the polymer comprising the active agent; cooling the cured polymer comprising the active agent; washing the composition with an organic solvent; and sterilizing the composition.

In embodiments, the present disclosure provides a method of preparing an ocular insert composition comprising a semi-crystalline or crystalline pharmaceutically active agent dispersed in a polymer matrix, the method including: dissolving the active agent in an organic solvent to form a solution; mixing the solution with a polymer; removing the organic solvent; curing the polymer comprising the active agent; cooling the cured polymer comprising the active agent; washing the composition with an organic solvent; and sterilizing the composition. In embodiments, the present disclosure includes a method of preparing an ocular insert composition comprising a semi-crystalline or crystalline pharmaceutically bimatoprost dispersed in a polymer matrix, the method including: dissolving bimatoprost in an organic solvent to form a solution; mixing the solution with a polymer; removing the organic solvent; curing the polymer comprising bimatoprost; cooling the cured polymer comprising bimatoprost; washing the composition with an organic solvent; and sterilizing the composition. In embodiments, the method of preparing the ocular insert of the present disclosure includes washing with an organic solvent, e.g., acetonitrile. In embodiments, the washing the insert with acetonitrile is for less than 48 hours. For example, in embodiments, the washing the insert with acetonitrile is for equal to or less than 8 hours. For example, in embodiments, the washing the insert with acetonitrile is for equal to or less than 6 hours. For example, in embodiments, the washing the insert with acetonitrile is for equal to or less than 4 hours. In embodiments, the washing the insert is at less than 60° C. In embodiments, the washing the insert is at about room temperature. The method of preparing the ocular insert of the present disclosure includes curing the disclosed composition at a temperature equal to or above about 65° C. For example, in embodiments, the composition is cured at a temperature equal to or above about 150° C. In embodiments, the method of preparing the ocular insert of the present disclosure includes sterilizing the composition with e-beam, gamma irradiation, or chemical treatment (e.g., ethylene oxide, ozone, peroxide vapor and/or chlorine dioxide). In embodiments, the method of preparing the ocular insert of the present disclosure produces equal to or less than about 2% degradation products of the bimatoprost comprising 5-trans bimatoprost and/or 15-keto bimatoprost. For example, in embodiments, equal to or less than about 1% 15-keto bimatoprost is formed. In embodiments, the method of preparing the ocular insert of the present disclosure includes preparing a ring-shaped ocular insert, which includes a polymer matrix including a thermosetting polymer or a thermoplastic polymer. For example, in embodiments, the thermosetting polymer is silicone. For example, in embodiments, the silicone is liquid silicone rubber, e.g., MED-4810, MED-4820, MED-4830, MED-4840, MED-4842, MED1-4855, MED-4860, MED-4870, MED-4880, or equivalents thereof. In embodiments, the active agent in the polymer matrix is chemically stable in the semi-crystalline or crystalline form for 760 days. In embodiments, the active agent in the polymer matrix is chemically stable in the semi-crystalline or crystalline form for 18 months, 12 months, 6 months, or 3 months.

In embodiments, the present disclosure provides a method of lowering intraocular pressure comprising placement of the composition as disclosed herein on or in an eye of a subject in need thereof.

In embodiments, the present disclosure provides a method of treating a disease or disorder of an eye of a subject in need thereof with an ocular insert comprising the composition of as disclosed herein.

Other features and advantages of the invention will be apparent from the following detailed description and claims.

Unless noted to the contrary, all publications, references, patents and/or patent applications reference herein are hereby incorporated by reference in their entirety for all purposes.

DETAILED DESCRIPTION OF THE DISCLOSURE

Figure 1:
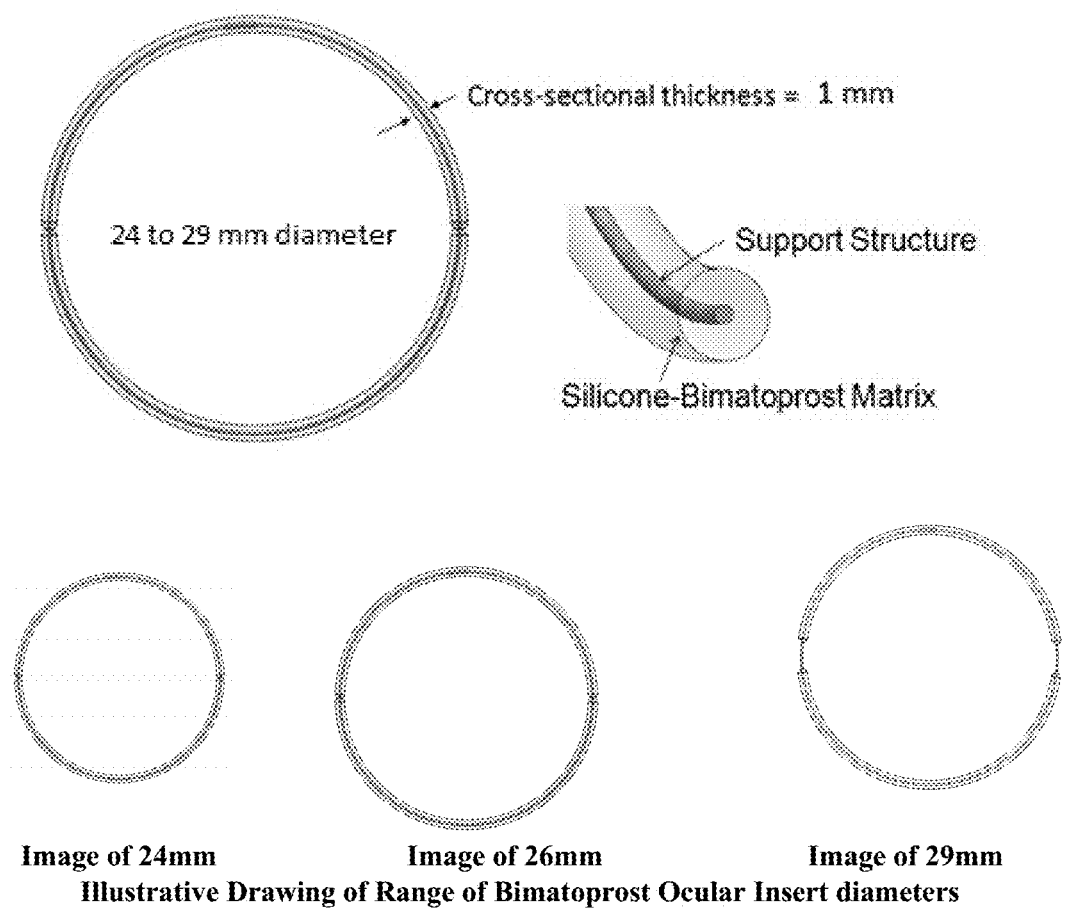
FIG. 1 shows an embodiment of the ocular device of the present invention and its cross-sectional view. Three different sizes of the device are also depicted.

Provided herein are, inter alia, compositions, methods, and kits of the present disclosure. In some aspects, the present disclosure includes compositions of an active agent dispersed in a polymer matrix. In some aspects, the present disclosure includes methods of preparing compositions of active agent dispersed in a polymer matrix, and methods of reducing or preventing degradation of the active agent in the composition. In some aspects, the present disclosure includes kits including a composition, e.g., an ocular insert composition, in which an active agent is dispersed in a polymer matrix.

The following definitions are included for the purpose of understanding the present subject matter and for constructing the appended patent claims. Abbreviations used herein have their conventional meaning within the chemical and biological arts.

DEFINITIONS

As used herein, the term "bimatoprost" refers to 7-[3,5-dihydroxy-2-(3-hydroxy-5-phenyl-pent-1-enyl)-cyclopentyl]-N-ethyl-hept-5-enamide:

Formula I

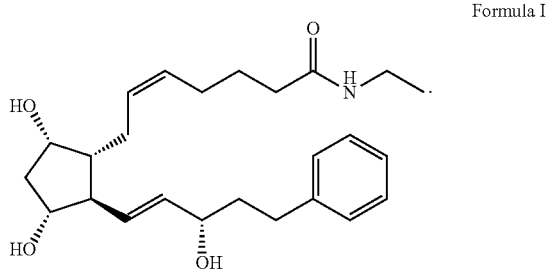 [SMILES: CCNC(=O)CCC/C=C\C[C@@H]1[C@@H](/C=C/[C@@H](O)CCc2ccccc2)[C@H](O)C[C@@H]1O]

Bimatoprost is the active ingredient in a product marketed by Allergan as an ophthalmic solution called LUIMIGAN®. It is also the active ingredient in a cosmetic formulation marketed by Allergan known as LATISSE®. The synthesis and purification of bimatoprost is described, e.g., in U.S. Pat. No. 7,157,590.

As used herein, the terms "cure," "curing," and "cured" refer to the toughening or hardening of a polymer material by cross-linking of polymer chains, brought about by chemical additives, ultraviolet radiation, electron beam (e-beam) or heat. In one aspect, the polymer is silicone.

As used herein, the term "process," "processing," and "processed" refer to reforming intermolecular interactions to remold thermoplastics. Processing is usually achieved by heating and cooling thermoplastics.

As used herein, the term "silicone" refers to polysiloxanes. In one aspect, the silicone has two parts or components, e.g., Part A and Part B, component A or component B. For example, Part A (or component A) may comprise of silica (e.g., about 20% silica). Part B (or component B) may comprise of silica (e.g., about 20% silica) and poly(dimethylsiloxane-co-methylhydrosiloxane) (e.g., less than about 3% and where the poly(dimethylsiloxane-co-methylhydrosiloxane) is trimethylsilyl terminated). In another aspect, silicone is liquid silicone rubber from NuSil Technology or Polymer Systems Technology, Ltd. under a catalog number of the MED-4800 series (e g. MED-4810, MED-4810 Part A, MED-4810 Part B, MED-4820, MED-4830, MED-4840, MED-4842, MED1-4855, MED-4860, MED-4870, MED-4880, or equivalents thereof). The liquid silicone rubber is a two-part, translucent silicone system, with 1:1 mix ratio (Part A:Part B).

As used herein, the term "medical device" refers to a drug-delivery system or device that affects or controls the release and/or delivery of the therapeutic agent in a certain way(s).

As used herein, the terms "ocular insert" and "ocular device" refer to a drug-impregnated device, whose size and shape are designed for ophthalmic application. See, e.g., Kumari A. et al., *J. Adv. Pharm. Technol. Res.* 2010, 1(3): 291-296. In one aspect, the insert may be sterile, thin, multilayered, drug-impregnated, solid or semisolid consistency. In another aspect, the insert may be placed into the cul-de-sac or conjunctival sac. Manufacturing and administration of various ocular inserts have been described in the literature. See, e.g., Kumari A. et al. *J. Adv. Pharm. Technol. Res.* 2010, 1(3): 291-296. In one aspect, the insert or device may be sterile, thin, multilayered, drug-impregnated, solid or semisolid consistency. In another aspect, the insert may be placed into the cul-de-sac or conjunctival sac.

As used herein "crystalline" means that the compound is crystallized into a specific crystal packing arrangement in three spatial dimensions or the compound having external face planes. Compounds in the crystalline state exhibit distinct sharp peaks in their X-ray diffraction patterns and typically exhibit well defined melting points. For example, bimatoprost can crystallize into different crystal packing arrangements, all of which have the same elemental composition of bimatoprost. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystals of bimatoprost may be prepared by crystallization under different conditions, e.g., different solvents, temperatures, etc. In embodiments, crystalline active agent may be at least 98% (w/w %) in crystalline form in a composition or the total active agent in the composition.

As used herein "semi-crystalline" means an active agent is in partially crystalline form. In embodiments, the semi-crystalline means the percentage of an active agent in crystalline form may be from between about 87% (w/w %) to about 98% (w/w %) in a composition or about 46% (w/w %) to about 98% (w/w %) of the total active agent in the composition.

As used herein "amorphous" or "non-crystalline" means that the compound does not exhibit any substantial peaks in its X-ray diffraction pattern. Typically, non-crystalline materials do not exhibit well defined melting points. In embodiments, the term "amorphous" means the active agent may be in non-crystalline form at least about 13% (w/w %) in the composition or at least about 66% (w/w %) of the total active agent in the composition.

All percentages and ratios used herein, unless otherwise indicated, are by weight.

As used in the context of the composition of the present disclosure the term "reducing", "reduce", or "reduction" means smaller or less in amount, degree, or size of an undesirable effect.

As used in the context of the composition of the present disclosure the term "preventing", "prevent", or "prevention" means keep (an undesirable effect) from happening or arising.

As used in the context of the composition of the present disclosure the term "degradation" means a process by which an active agent in the composition changes physical and/or functional properties. For example, the chemical nature and/or properties of an active agent are/is altered such that the altered products are not desirable in the composition.

As used in the context of the composition of the present disclosure the term "dispersed" means an active agent is distributed or spread over a wide area. In embodiments, an active agent may be distributed or spread over non-uniformly over a wide area a composition, e.g., ocular insert composition.

As used in the context of the composition of the present disclosure the term "impurities" means—in part—degradation by-products of the active agent. The term "impurities" may also include compounds, intermediates of a method of preparation, undesirable amounts of additives and excipients and by-products of these during a method of preparation of a composition.

As used in the context of the composition of the present disclosure the term "washing" means rinsing, dipping, soaking, wetting thoroughly, drenching, suffusing, flowing along, causing to swirl, or any other means which would be understood by an ordinary skilled person as "washing."

As used in the context of the composition of the present disclosure the term "stable" means physical and chemical stability. Chemical stability relates to changes to an active substance itself, e.g., degradation products of the active agent. In embodiments of the present disclosure, storage or shelf-life of a composition is a measure of chemical stability. Physical stability relates to mechanical properties, physical state (e.g., crystallinity, crystal structure), and active agent (or drug) release properties. In embodiments of the present disclosure, the physical stability correlates with the day 1 burst release or elution of an active agent from the composition, e.g., ocular insert composition in which an active agent, e.g., bimatoprost, is dispersed in a polymer matrix.

As used in the context of the composition of the present disclosure the term "polymer matrix" means polymer matrix including of a variety of short or continuous fibers of an organic polymer bound together. Thermosetting polymer matrix and thermoplastic polymer matrix are well known in the art. Thermosets are solidified by irreversible chemical reactions, in which the molecules in the polymer "cross-link," or form connected chains. Thermoplastics, on the other hand, are melted and then solidified, a process that can be repeated numerous times for reprocessing.

Although specific reference is made to a ring-shaped ocular insert, medical devices or apparatus having different features can be prepared and used according to the known methods. Such embodiments are within the scope of this invention. For example, U.S. Ser. No. 13/618,052, U.S. Ser. No. 13/688,019, and WO2013/040426, specifically incorporated by reference herein, describe many embodiments of an ocular insert that can be comfortably placed at many locations of the conjunctiva, including along at least a portion of the conjunctival sac. The insert can move when placed on the conjunctiva and can be retained with the eye so as to provide improved comfort for the patient. The insert may comprise a resistance to deflection to retain the insert comfortably within the eye. The insert can be configured in many ways to provide the resistance to deflection. The insert may comprise a matrix comprising the resistance to deflection, and the matrix may comprise a material providing the resistance to deflection. Alternatively or in combination, the insert may comprise a retention structure and a support structure coupled to the retention structure, in which the support structure may contain the therapeutic agent. The retention structure may comprise an inner structure with the support structure comprising the therapeutic agent covering at least a portion of the retention structure, or the retention structure may comprise an outer structure covering at least a portion of the support structure comprising the therapeutic agent.

The insert may be configured such that the insert can be deflected during insertion and removal and may comprise the resistance to deflection for comfort and retention. The insert comprising the resistance to deflection can be comfortably placed at one or more of many locations of the conjunctiva, such that many patients can be treated comfortably and the placement can be adjusted based on the anatomy of the patient and physician preference. The insert may comprise the resistance to deflection such that the conjunctiva can be shaped with the insert so as to receive the insert, and in many embodiments the insert may comprise an amount of resistance to form one or more of a fold, a pocket, or deformation of the conjunctiva so as to receive and retain the insert. The one or more locations where the insert can be placed include the inferior conjunctival sac, an inferior temporal location of the conjunctival sac, an inferior nasal location of the conjunctival sac, the superior conjunctival sac, portions of the upper and lower conjunctival sacs near lateral canthus of the palpebral fissure, portions of the upper and lower conjunctival sacs near the medial canthus and caruncle. These areas are well suited to receive structures having relatively large volumes for extended release of one or more therapeutic agents. In one embodiment, the ocular insert is positioned on a region outside an optical zone of an eye.

The insert can be configured in many ways to treat a patient with bimatoprost for an extended time, and may comprise one or more of a high dose of therapeutic agent, a substantial surface area to release the therapeutic agent, a hoop strength to resist deflection, a bending strength to resist deflection, a shape profile to fit the eye, or a biasing curve to retain the insert, and combinations thereof. The insert may comprise biasing shape so as to retain the insert, for example with a curve, bend, or other deflected shape to retain the insert. The biasing shape may comprise a resiliently curved biasing spring structure shaped to provide force in response to deflection so as to urge one or more of the first portion or the second portion toward the eye to retain the insert.

The insert can be sized and shaped for placement under the eyelids and along at least a portion of a conjunctival sac of the upper and lower lids of the eye, or combinations thereof. The insert can be sized and shaped so as to move within the conjunctival sac of the eye and be held on the eye without attachment to the eye so as to provide improved comfort. The insert may comprise a preformed shape profile corresponding to a curved shape profile of the eye extending away from a plane, such that the insert can resist deflection away from bulbar conjunctiva toward the plane when placed. The insert can be configured to deflect when placed in the conjunctival sac of the eye and guide the insert along the sac when the eye moves with one or more of rotation or cyclotorsion. The insert may also comprise resistance to deflection so as to urge the insert outward and inhibit movement of the retention structure toward the cornea. The insert may comprise a first portion having a first resistance to deflection and a second portion having a second resistance to deflection less than the first portion, such that first portion can resist deflection of the upper lid and the second portion can fit within the one or more folds of the lower lid. The first portion and the second portion may comprise a similar material, and the first portion may have a cross sectional size greater than the second portion to provide the increased resistance to deflection, and the increased cross sectional size of the first portion may help to retain the first portion with the upper lid. Alternatively or in combination, the increased cross-sectional size of the first portion may provide anchoring under the upper lid. The insert may move rotationally with deflection along the conjunctival sac such that the retention structure can slide along the conjunctival sac about an axis of rotation passing through the iris and the pupil of the eye. In many embodiments the insert can allow sliding movement along the conjunctiva in response to torsional or other movement of the eye so as to improve comfort for the patient.

The insert can be configured in many ways to provide the resistance to deflection. The insert may comprise a retention structure providing a majority of the resistance to deflection. Alternatively, the insert can be configured to provide the resistance to deflection without a retention structure, and in many embodiments may comprise with a active agent (drug) delivery matrix configured to provide the resistance to deflection such that the insert can be provided without the retention structure.

The retention structure can be configured in many ways to provide increased comfort for the patient, and can be placed in many ways. The retention structure may comprise soft material at locations corresponding to one or more of the lacrimal gland or the caruncle, and can be shaped to inhibit contact with tissue near one or more of the lacrimal gland or the caruncle. Although the retention structure may comprise one or more of many shapes such as circular, oval, serpentine, saddle shaped, cylindrical or toric, the retention structure may comprise one or more portions shaped to inhibit irritation to the lacrimal gland and the caruncle. The retention structure can be shaped to inhibit contact with the conjunctiva covering the lacrimal gland, and the retention structure may comprise an extension shaped to extend around the lacrimal gland. The extension can extend inward toward the pupil around the lacrimal gland, or outward away from the pupil around the lacrimal gland. The retention structure may comprise a portion shaped to extend away from the caruncle when placed, such as an inward extension.

"Treating", includes any effect, e.g., lessening, reducing, modulating, preventing, or eliminating, that results in the improvement of the condition, disease, disorder, etc. "Treating" or "treatment" of a disease state includes: (1) inhibiting the disease state, i.e., arresting the development of the disease state or its clinical symptoms; (2) relieving the disease state, i.e., causing temporary or permanent regression of the disease state or its clinical symptoms; (3) reducing or lessening the symptoms of the disease state; or (4) preventing the disease state, e.g., causing the clinical symptoms of the disease state not to develop in a subject that may be exposed to or predisposed to the disease state, but does not yet experience or display symptoms of the disease state. As used herein, "preventing" or "prevent" describes reducing or eliminating the onset of the symptoms or complications of the disease, condition or disorder. The term "preventing," when used in relation to a condition, such as intraocular pressure, is art-recognized, and refers to formulation, composition and/or device (e.g., ocular insert) which reduces the frequency of, or delays the onset of, signs and/or symptoms of a medical condition in a subject relative to a subject which does not receive the composition.

As used herein, the term "alleviate" is meant to describe a process by which the severity of a sign or symptom of a disorder is decreased. Importantly, a sign or symptom can be alleviated without being eliminated.

As used herein the term "symptom" is defined as an indication of disease, illness, injury, or that something is not right in the body.

As used herein the term "sign" is defined as an indication that something is not right in the body. Signs are defined as things that can be seen by a doctor, nurse, or other health care professional.

The term "about" is used herein to mean approximately, in the region of, roughly or around. When the term "about" is used in conjunction with a numerical range, it modifies that range by extending the boundaries above and below the numerical values set forth. In general, the term "about" is used herein to modify a numerical value above and below the stated value by a variance of 20%.

As used in the present disclosure, whether in a transitional phrase or in the body of a claim, the terms "comprise(s)" and "comprising" are to be interpreted as having an open-ended meaning. That is, the terms are to be interpreted synonymously with the phrases "having at least" or "including at least." When used in the context of a process the term "comprising" means that the process includes at least the recited steps, but may include additional steps. When used in the context of a molecule, compound, or composition, the term "comprising" means that the compound or composition includes at least the recited features or components, but may also include additional features or components.

For the purposes of promoting an understanding of the embodiments described herein, reference made to preferred embodiments and specific language are used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. All percentages and ratios used herein, unless otherwise indicated, are by weight.

The term "more" as used in the present disclosure does not include infinite number of possibilities. The term "more" as used in the present disclosure is used as a skilled person in the art would understand in the context in which it is used. For example, more than "36 months" implies, as a skilled artisan would understand, 37 months or the number of months the ocular insert can be or is used by a subject, which is greater than 36 months, without loss of efficacy of the therapeutic agent in the insert.

Unless otherwise defined, all technical and scientific terms used herein have the same meaning as commonly understood by one of ordinary skill in the art to which this invention belongs. In the case of conflict, the present specification will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Compositions

Provided herein are compositions of semi-crystalline or crystalline pharmaceutically active agents and a polymer. In aspects of this disclosure, the polymer forms a matrix, and the semi-crystalline or crystalline pharmaceutically active agents ("active agent(s)") are dispersed in the polymer matrix. In aspects of this disclosure, the compositions are ocular compositions, e.g., ocular insert compositions. In aspects of this disclosure, the active agent is bimatoprost.

The term "pharmaceutical composition" includes preparations suitable for administration to mammals, e.g., humans. When an active agent of the present disclosure is provided to mammals, e.g., humans, the agent may be given as an ocular composition, e.g., an ocular insert including, e.g., about 1% to about 25% of the active agent in combination with a pharmaceutically acceptable carrier.

In embodiments, a composition of the present disclosure includes an active agent, e.g., bimatoprost, about 0.1% to about 40% by weight of the composition, about 1% to about 30% by weight of the composition, about 2% to about 30% by weight of the composition, about 2% to about 25% of the composition, or about 2% to about 22% by weight of the compositions. In embodiments, the active agent, e.g., bimatoprost, is about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, or about 22% by weight of the composition. In embodiments, the present disclosure includes a composition, e.g., an ocular insert composition, including about 20% by weight of an active agent, e.g., bimatoprost, of the composition.

In embodiments, a composition of the present disclosure, e.g., an ocular insert composition, includes a semi-crystalline form of an active agent, e.g., bimatoprost. In embodiments, a composition of the present disclosure, e.g., an ocular insert composition, including a semi-crystalline form of an active agent, e.g., bimatoprost, may have equal to or less than about 5% impurities, e.g., 15-keto bimatoprost. In embodiments, a composition of the present disclosure, e.g., an ocular insert composition, including a semi-crystalline form of an active agent, e.g., bimatoprost, may have equal to or less than about 5%-about 4%, about 4%-about 3%, about 3%-about 2%, about 2%-about 1%, impurities, e.g., 15-keto bimatoprost. In embodiments, the composition of the present disclosure includes about 1% 5-trans bimatoprost and about 1% 15-keto bimatoprost.

In embodiments, a composition of the present disclosure, e.g., an ocular insert composition, includes a crystalline form of an active agent, e.g., bimatoprost. In embodiments, a composition of the present disclosure, e.g., an ocular insert composition, including a crystalline form of an active agent, e.g., bimatoprost, may have equal to or about 0.5% or less (e.g., about 0.0%-about 0.1%, about 0.1%-about 0.2%, about 0.2%-about 0.3%, about 0.3%-about 0.4%, about 0.4%-about 0.5%) impurities, e.g., 15-keto bimatoprost.

In embodiments, the compositions of the present disclosure include impurities such as 15-keto bimatoprost. In embodiments, the compositions of the present disclosure include equal to or about 0.3% or less (e.g., about 0.0%-about 0.1%, 0.1%-about 0.2%, about 0.2%-about 0.3%) 15-keto bimatoprost.

In embodiments, the compositions of the present disclosure include equal to or about 0.3% 15-keto bimatoprost. In embodiments, the compositions of the present disclosure include less than about 0.3% 15-keto bimatoprost.

In embodiments, the compositions of the present disclosure include impurities such as 5-trans bimatoprost. In embodiments, the compositions of the present disclosure include equal to or about 0.1% to about 0.2% 5-trans bimatoprost.

In embodiments, the compositions of the present disclosure include about 0.1% 5-trans bimatoprost and about 0.3% 15-keto bimatoprost.

In embodiments, the compositions of the present disclosure include about 0.2% 5-trans bimatoprost and about 0.3% 15-keto bimatoprost.

In embodiments, the compositions of the present disclosure include semi-crystalline or crystalline bimatoprost that is stable in the composition for 730 or more days, e.g., 760 days. In embodiments, ocular inserts comprising bimatoprost and thermoplastic polymer of the present disclosure have a shelf life or stability of about 18 months to about 36 months or more.

The stability is measured after storing the ocular inserts of the current disclosure in a humidity chamber with a relative humidity (RH) of about 60% to about 75%, and temperature of about 25° C.±2° C. to about 40° C.±2° C. For example, the accelerated stability data is measured at about 40° C.±2° C. under about 75% relative humidity (RH). Accelerated aging parameters, including information that validates the accelerated system are required for product shelf-life testing. Real time testing of shelf life is also performed in order to confirm the tentative shelf life data collected from the accelerated tests. In addition, the shelf life of ocular inserts is also tested under expected packaging conditions, for example when the ocular inserts are packaged in the presence of an oxygen absorber. Tensile strength is also tested under accelerated conditions (high temperature and relative humidity).

In embodiments, the polymer matrix of the present disclosure include a thermosetting polymer or a thermoplastic polymer. In embodiments, the thermosetting polymer is silicone. In embodiments, the silicone is liquid silicone rubber, e.g., MED-4810, MED-4820, MED-4830, MED-4840, MED-4842, MED1-4855, MED-4860, MED-4870, MED-4880, or equivalents thereof.

Other examples of suitable thermosetting polymers include, but are not limited to, polyesters (e.g. PET), polyurethanes, vulcanized rubbers, urea-formaldehyde, melamine, epoxy, polyimides, cyanate esters (polycyanurates), vinylesters, bakelite (a phenol-formaldehyde), and duroplast (similar to bakelite).

Examples of thermoplastic polymer include, but are not limited to, acrylonitrile butadiene styrene (ABS), acrylic (PMMA), celluloid, cellulose acetate, cycloolefin copolymer (COC), ethylene-vinyl acetate (EVA), ethylene vinyl alcohol (EVOH), fluoroplastics (PTFE, alongside with FEP, PFA, CTFE, ECTFE, ETFE), ionomers, Kydex, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC), and styrene-acrylonitrile (SAN).

In embodiments, the compositions of the present disclosure are configured as a device, e.g., a medical device. In embodiments, the compositions of the present disclosure are configured as an ocular insert. In embodiments, the ocular insert is a ring shaped ocular insert. The ocular insert is intended to be placed or suitable for placement on or in the eye. In embodiments, the largest dimension (e.g., diameter) of the ring may be about 10 mm to about 40 mm or about 20 mm to about 30 mm (e.g., about 20 mm, about 21 mm, about 22 mm, about 23 mm, about 24 mm, about 25 mm, about 26 mm, about 27 mm, about 28 mm, about 29 mm, or about 30 mm) and the cross-sectional thickness can be 0.1 mm to about 5 mm or about 0.5 mm to about 1.5 mm (e.g., about 0.5 mm, about 0.6 mm, about 0.7 mm, about 0.8 mm, about 0.9 mm, about 1 mm, about 1.1 mm, about 1.2 mm, about 1.3 mm, about 1.4 mm, or about 1.5 mm). FIG. 1 demonstrates an embodiment of the ring-shaped insert.

In embodiments, the V501 Bimatoprost Ocular Insert is a sterile, preservative-free, single use sustained release drug product containing about 13 mg bimatoprost in MED-4830 silicone or equivalents thereof. In embodiments, the Insert has a ring configuration consisting of two off-white drug-containing silicone segments structurally supported with a polypropylene monofilament. In embodiments, thickness (cross-section) of the Insert is about 1 mm with sizes ranging from 24 mm to 29 mm in diameter to allow for different sizes of eyes in clinical use, as shown in FIG. 1. In embodiments, V501 Bimatoprost Ocular Inserts contain the same drug content irrespective of size.

In embodiments, the bimatoprost Ocular Insert is composed of two silicone-bimatoprost tubes placed over a support structure which is fused into a ring shape, as shown in FIG. 1. In embodiments, bimatoprost is dispersed into the silicone and molded and cured in the shape of tubes that are 1 mm in diameter. In embodiments, two tubes are then threaded over a support structure. In embodiments, the support structure includes commercially available polypropylene monofilament that has been cut to length and heat-set into a ring shape. In embodiments, the molded tubes of silicone-drug matrix are threaded over the polypropylene, and the polypropylene monofilament ends are then fused together to form the ring. Each ring contains about 13 mg of bimatoprost. In embodiments, each Bimatoprost Ocular Insert is placed in a packaging tray and terminally sterilized by e-beam irradiation, gamma irradiation, or chemical treatment (e.g., ethylene oxide, ozone, peroxide vapor, and/or chlorine dioxide). In embodiments, the storage condition for the drug product is room temperature (about 15-30° C.).

In an embodiment, the ocular ring of the present disclosure has a largest dimension (e.g., diameter) of about 10 mm to about 40 mm and a cross-sectional thickness of about 0.1 mm to about 5 mm. In an embodiment, the ocular ring of the present disclosure has a largest dimension (e.g., diameter) of about 20 mm to about 30 mm and the cross-sectional thickness is about 0.5 mm to about 1.5 mm.

In embodiments, the compositions of the present disclosure may include one or more second therapeutic agent. Examples of such an agent include, but are not limited to, a muscarinic agent, a beta blocker, an alpha agonist, a carbonic anhydrase inhibitor, another prostaglandin analog, an anti-inflammatory agent, an anti-infective agent, a dry eye medication, or any combination thereof. See, e.g., U.S. Patent Application Publication 2009/0104243. In one embodiment, the secondary therapeutic agent used in an ocular insert comprising a polymer matrix and crystalline or semi-crystalline bimatoprost is Loteprednol (loteprednol etabonate) and/or Timolol (Timolol maleate).

In embodiments, the second therapeutic agent included in the compositions of the current disclosure may be an anti-hypertensive agent. Examples of anti-hypertensive therapeutic agents include: sympathomimetics such as Apraclonidine, Brimonidine, Clonidine, Dipivefrine, and Epinephrine; parasympathomimetics such as Aceclidine, Acetylcholine, Carbachol, Demecarium, Echothiophate, Fluostigmine, Neostigmine, Paraoxon, Physostigmine, and Pilocarpine; carbonic anhydrase inhibitors such as Acetazolamide, Brinzolamide, Diclofenamide, Dorzolamide, and Methazolamide, beta blocking agents such as Befunolol, Betaxolol, Carteolol, Levobunolol, Metipranolol, and Timolol; additional prostaglandin analogues such as Latanoprost, Travoprost, and Unoprostone; and other agents such as Dapiprazole, and Guanethidine.

In embodiments, the secondary agent for delivery from the ocular insert of the present disclosure may include, e.g., without being limiting, the following or their equivalents, derivatives or analogs: thrombin inhibitors; antithrombogenic agents; thrombolytic agents; fibrinolytic agents; vasospasm inhibitors; vasodilators; antihypertensive agents; antimicrobial agents, such as Benzalkonium (BAK) or antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; anti-platelet agents; antimitotics; microtubule inhibitors; antisecretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); and non-steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Such anti-inflammatory steroids contemplated for use in the methodology of the embodiments described here, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, —estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, anti-prostaglandins, prostaglandin precursors, including antiglaucoma drugs including beta-blockers such as Timolol, betaxolol, levobunolol, atenolol, and additional prostaglandin analogues such as travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

In embodiments, the compositions of the present disclosure may also include additives or excipients. For example, the compositions may contain an inert filler material, a salt, a surfactant, a dispersant, a second polymer, a tonicity agent, or a combination thereof. See, e.g., U.S. Patent Application Publication 2009/0104243.

In embodiments, additives and/or excipients in the ocular insert including a polymer matrix and crystalline or semi-crystalline bimatoprost includes a phospholipid (e.g., 1,2-dimyristoyl-sn-glycero-3-phosphocholine (DMPC)), stearyl alcohol, and/or carbopol.

Methods of Reducing or Preventing Degradation of Active Agent

Provided herein is a method of reducing or preventing degradation of a semi-crystalline or crystalline pharmaceutically active agent dispersed in a polymer matrix in an ocular insert composition, the method including washing the insert with an organic solvent. In embodiments, the ocular insert of the present disclosure is washed before it is sterilized during preparation of the composition.

In embodiments, the method of reducing or preventing degradation reduces or prevents degradation of a semi-crystalline or crystalline bimatoprost. In embodiments, the present disclosure includes a method of reducing or preventing degradation of a semi-crystalline or crystalline pharmaceutically active agent, e.g., bimatoprost, dispersed in a polymer matrix in a ring shaped ocular insert. In embodiments, the method reduces or prevents degradation of a semi-crystalline or crystalline bimatoprost to 5-trans bimatoprost and/or 15-keto bimatoprost.

In embodiments, the present disclosure includes a method of reducing or preventing degradation of a semi-crystalline or crystalline pharmaceutically active agent, e.g., bimatoprost, dispersed in a thermosetting or thermoplastic polymer matrix in a ring shaped ocular insert. In embodiments, the thermosetting polymer may be silicone. In embodiments, silicone is liquid silicone rubber, e.g., MED-4810, MED-4820, MED-4830, MED-4840, MED-4842, MED1-4855, MED-4860, MED-4870, MED-4880, or equivalents thereof.

In embodiments, the present disclosure includes a method of reducing or preventing degradation of a semi-crystalline or crystalline pharmaceutically active agent, e.g., bimatoprost, dispersed in a polymer matrix in an ocular insert composition, the method including washing the insert with an organic solvent, for example acetonitrile. In embodiments, the method includes washing the insert with an organic solvent, for example acetonitrile, for less than 48 hours. In embodiments, the method includes washing the insert with acetonitrile for equal to or less than 8 hours. In embodiments, the method includes washing the insert with acetonitrile for equal to or less than 6 hours. In embodiments, the method includes washing the insert with an organic solvent, for example acetonitrile, for equal to or less than 4 hours.

In embodiments, the present disclosure includes a method of reducing or preventing degradation of a semi-crystalline or crystalline pharmaceutically active agent, e.g., bimatoprost, dispersed in a polymer matrix in an ocular insert composition, the method including washing the insert with an organic solvent, for example acetonitrile, at less than about 60° C. In embodiments, the method includes washing the insert is at about room (or ambient) temperature, e.g., about 15° C. to about 30° C.

In embodiments, the present disclosure includes a method of reducing or preventing degradation of a semi-crystalline or crystalline pharmaceutically active agent, e.g., bimatoprost, dispersed in a polymer matrix, e.g., a thermosetting polymer or a thermoplastic polymer, in an ocular insert composition, the method including washing the insert with an organic solvent, e.g., acetonitrile. Examples of the polymers are described in detail in the above section.

In an embodiment, the method of reducing or preventing degradation of the active agent, e.g., bimatoprost, in the composition, e.g., ocular insert composition, of the present disclosure does not include washing the composition with water. In an embodiment, the method of improving stability of the active agent, bimatoprost, in the composition, e.g., ocular insert composition, of the present disclosure does not include washing in a solvent that causes the composition to swell significantly, for example dichloromethane or isopropanol.

Methods of Increasing/Improving Stability

Provided herein are methods of increasing or improving stability of a semi-crystalline or crystalline pharmaceutically active agent dispersed in a polymer matrix in an ocular insert composition, the method including washing the insert with an organic solvent. In embodiments, the ocular insert of the present disclosure is washed before it is sterilized during preparation of the composition.

In embodiments, the methods of the present disclosure include washing an ocular insert composition including a semi-crystalline or crystalline active agent, e.g., bimatoprost, dispersed in a polymer matrix, with an organic solvent, e.g., acetonitrile, in which the washing chemically stabilizes (chemical stability relates to changes to the active substance itself (degradation products)), the active agent in the insert for about 730 or more days, e.g., 760 days. In embodiments, the chemical stability, i.e., storage stability (chemical stability relates to changes to the active substance itself (degradation products)), may be equal to or up to 760 days. In embodiments, the chemical stability, i.e., storage stability (chemical stability relates to changes to the active substance itself (degradation products)), may be equal to or up to 24 months, 18 months, 12 months, or 6 months. In embodiments, an ocular insert composition including a semi-crystalline or crystalline active agent, e.g., bimatoprost, dispersed in a polymer matrix that is washed with an organic solvent, e.g., acetonitrile, during testing/preparation may be stored at room temperature (ambient temperature) or at accelerated temperature conditions, for example 40° C.

In embodiments, the physical stability of the active agent in the polymer matrix is increased/improved such that the mechanical properties, physical state (crystallinity, crystal structure), and active agent release properties of the ocular insert prevents the increase in the burst release/elution of the active agent on day 1. Active agent release rate testing of unwashed inserts have shown a high day 1 burst (equal to or more than about 70 µg/day) of active agent/drug (initial release). In embodiments of the present disclosure, this burst may be circumvented by washing the inserts prior to packaging and sterilization, which removes the outer layer of the active agent. In embodiments, the present disclosure includes wash conditions by which a burst of equal to or less than about 60 µg of active agent release on day 1 is achieved. In embodiments, the present disclosure provides wash conditions with an organic solvent, e.g., acetonitrile, by which a day 1 burst of equal to or less than about 60 µg of active agent release on day 1 is achieved. In embodiments, the present disclosure provides wash conditions with an organic solvent, e.g., acetonitrile, by which a day 1 burst of equal to or less than about 59 µg-55 µg, about 55 µg-50 µg, about 50 µg-45 µg, about 45 µg-40 µg, about 40 µg-35 µg, or about 35 µg-30 µg of active agent release on day 1 is achieved.

Method of Preparing an Ocular Insert Composition

Provided herein is a method of preparing an ocular insert composition including a semi-crystalline or crystalline pharmaceutically active agent, e.g., bimatoprost, dispersed in a polymer matrix, the method including: mixing the active agent with a polymer; curing the polymer including the active agent; cooling the cured polymer including the active agent; washing the composition with an organic solvent, e.g., acetonitrile; and sterilizing the composition. In embodiments, the curing is done at a temperature equal to or above about 65° C. For example, in embodiments the curing may be done at a temperature of about 150° C. In embodiments, the sterilizing the composition is with e-beam, gamma irradiation, or chemical treatment (e.g., ethylene oxide, ozone, peroxide vapor, and/or chlorine dioxide). In embodiments, the method includes washing the insert with acetonitrile for less than 48 hours. In embodiments, the method includes washing the insert with acetonitrile for equal to or less than 8 hours. In embodiments, the method includes washing the insert with acetonitrile for equal to or less than 6 hours. In embodiments, the method includes washing the insert with acetonitrile for equal to or less than 4 hours. In embodiments, the method includes washing the insert with acetonitrile at less than 60° C. In embodiments, the method includes washing the insert with acetonitrile at about room (or ambient) temperature, e.g., about 15° C. to about 30° C.

Also provided herein is a method of preparing an ocular insert composition including a semi-crystalline or crystalline pharmaceutically active agent, e.g., bimatoprost, dispersed in a polymer matrix, the method including: dissolving the active agent in an organic solvent to form a solution; mixing the solution with a polymer; removing the organic solvent; curing the polymer including the active agent; cooling the cured polymer including the active agent; washing the composition with an organic solvent, e.g., acetonitrile; and sterilizing the composition. In embodiments, the curing is done at a temperature equal to or above about 65° C. For example, in embodiments the curing may be done at a temperature of about 150° C. In embodiments, the sterilizing the composition is with e-beam, gamma irradiation, or chemical treatment (e.g., ethylene oxide, ozone, peroxide vapor, and/or chlorine dioxide). In embodiments, the method includes washing the insert with acetonitrile for less than 48 hours. In embodiments, the method includes washing the insert with acetonitrile for equal to or less than 8 hours. In embodiments, the method includes washing the insert with acetonitrile for equal to or less than 6 hours. In embodiments, the method includes washing the insert with acetonitrile for equal to or less than 4 hours. In embodiments, the method includes washing the insert with acetonitrile at less than 60° C. In embodiments, the method includes washing the insert with acetonitrile at about room (or ambient) temperature, e.g., about 15° C. to about 30° C.

In embodiments, the present disclosure includes a method of preparing an ocular composition, e.g., ocular insert composition, including a semi-crystalline or crystalline pharmaceutically active agent, e.g., bimatoprost, dispersed in a polymer matrix, e.g., a thermosetting polymer or a thermoplastic polymer, the method including washing the insert with an organic solvent, e.g., acetonitrile. Examples of the polymers are described in detail in the above section.

In embodiments, the present disclosure includes a method of preparing a composition, e.g., a ring shaped ocular insert composition, including semi-crystalline or crystalline pharmaceutically active agent, e.g., bimatoprost, dispersed in a thermosetting or thermoplastic polymer matrix. In embodiments, the thermosetting polymer may be silicone. In embodiments, the silicone is liquid silicone rubber, e.g., MED-4810, MED-4820, MED-4830, MED-4840, MED-4842, MED1-4855, MED-4860, MED-4870, MED-4880, or equivalents thereof.

In an embodiment, the method of preparing a composition, e.g., ocular insert composition including bimatoprost dispersed in a polymer matrix, of the present disclosure does not include washing the composition with water. In an embodiment, the method of the present disclosure does not include washing the composition, e.g., ocular insert composition including bimatoprost dispersed in a polymer matrix, with dichloromethane or isopropanol.

In embodiments, the present disclosure provides a method of preparing an ocular insert composition including chemically and physically stable bimatoprost dispersed in a polymer matrix, the method including solubilizing bimatoprost in a solvent to prepare a bimatoprost solution, and mixing the bimatoprost solution with a polymer matrix, removing the solvent, curing the resulting polymer matrix at a temperature higher than the melting temperature of bimatoprost, cooling the composition, storing the composition at a temperature to allow recrystallization of bimatoprost, and washing with an organic solvent e.g., acetonitrile at a temperature below 60° C., and thereby preparing the ocular insert composition including chemically and physically stable bimatoprost.

In embodiments, the present disclosure provides a method of preparing an ocular insert composition including chemically and physically stable bimatoprost dispersed in a polymer matrix, the method including mixing solid bimatoprost with a polymer matrix, curing the resulting polymer matrix at a temperature higher than the melting temperature of bimatoprost, cooling the composition, storing the composition at a temperature to allow recrystallization of bimatoprost, and washing with an organic solvent e.g., acetonitrile at a temperature below 60° C., and thereby preparing the ocular insert composition including chemically and physically stable bimatoprost.

Kits

Provided herein are kits including an ocular insert in which a semi-crystalline or crystalline pharmaceutically active agent, e.g., bimatoprost, is dispersed in a polymer matrix.

In embodiments, the kits of the present disclosure include an ocular insert in which a semi-crystalline or crystalline pharmaceutically active agent, e.g., bimatoprost, includes equal to or about 2% or less (e.g., about 0.0%-about 0.1%, about 0.1%-about 0.2%, about 0.2%-about 0.3%, about 0.3%-about 0.4%, about 0.4%-about 0.5%, about 0.5%-about 1%, about 1%-about 2%) impurities.

In embodiments, the kits of the present disclosure include an ocular insert in which a semi-crystalline or crystalline pharmaceutically active agent, e.g., bimatoprost, includes impurities such as 15-keto bimatoprost. In embodiments, the kits of the present disclosure include an ocular insert in which a semi-crystalline or crystalline pharmaceutically active agent, e.g., bimatoprost, includes equal to or about 1% or less (e.g., about 0.0%-about 0.1%, 0.1%-about 0.2%, about 0.2%-about 0.3%, about 0.3%-about 1%) 15-keto bimatoprost. In embodiments, the kits of the present disclosure include an ocular insert in which a semi-crystalline or crystalline pharmaceutically active agent, e.g., bimatoprost, includes equal to or about 1% 15-keto bimatoprost.

In embodiments, the kits of the present disclosure include an ocular insert in which a semi-crystalline or crystalline pharmaceutically active agent, e.g., bimatoprost, includes equal to or about 0.1% to about 0.2% 5-trans bimatoprost. In embodiments, the kits of the present disclosure include an ocular insert in which a semi-crystalline or crystalline pharmaceutically active agent, e.g., bimatoprost, includes equal to or about 1% 5-trans bimatoprost.

In embodiments, the kits of the present disclosure include an ocular insert in which a semi-crystalline or crystalline pharmaceutically active agent, e.g., bimatoprost, includes about 0.1% 5-trans bimatoprost and about 0.3% 15-keto bimatoprost. In embodiments, the kits of the present disclosure include an ocular insert in which a semi-crystalline or crystalline pharmaceutically active agent, e.g., bimatoprost, includes about 0.2% 5-trans bimatoprost and about 0.3% 15-keto bimatoprost. In embodiments, the kits of the present disclosure include an ocular insert in which a semi-crystalline or crystalline pharmaceutically active agent, e.g., bimatoprost, includes equal to or about 1% 5-trans bimatoprost and equal to or about 1% 15-keto bimatoprost.

In embodiments, the kits of the present disclosure include instruction manual, buffers, reagents, containers and the like for placing and storing the ocular insert during storage on the shelf, transport, and before placing onto the eye of a subject.

Methods of Use in the Treatment of an Ocular Disease and/or Disorder

Provided herein is a method of lowering intraocular pressure comprising placement of the composition of the current disclosure, e.g., ocular insert, on or in an eye of a subject in need thereof.

Also provided herein is a method of treating a disease or disorder of an eye of a subject in need thereof with an ocular insert including a semi-crystalline or crystalline pharmaceutically active agent dispersed in a polymer matrix.

Figure 5A:
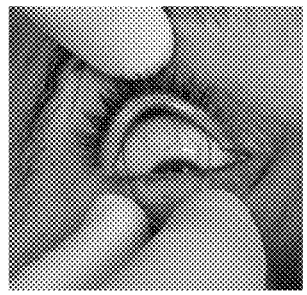
FIGS. 5A-C show the placement of the ocular device of the present disclosure in the eye of a subject.
Figure 5B:
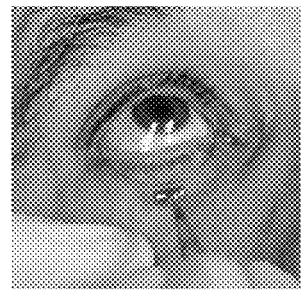
Figure 5C:
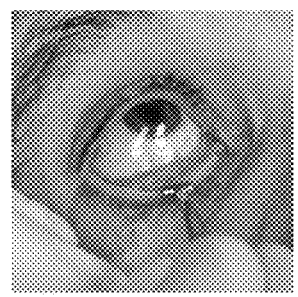

Compositions, e.g., ocular insert, of the present disclosure can be used to treat eye disease. The device having a ring shape as prepared above can be placed on or in an eye to reduce intraocular pressure. For example, following optional administration of a drop of anesthetic agent, the eyelids are gently spread open and, using either fingers or a blunt-ended surgical instrument, the ocular insert is placed in the upper and lower fornices, as shown in FIG. 5. The ocular device may be kept in place for a long period of time, during which time bimatoprost is continuously released to the eye at a therapeutically effective level so as to exert the sustained reduction of intraocular pressure. Such reduction in TOP can thereby decrease the rate of progression of the signs and symptoms of glaucoma.

In embodiments, the therapeutic active agent is bimatoprost. In embodiments, the active agent may be or may further include travoprost, latanoprost, tafluprost, NSAID, steroid, antihistamine, carbonic anhydrase inhibitor (CAI), dorzolamide, cyclosporine, antibiotic, doxycycline, tetracycline, azithromycin, fatty acid, long chain fatty acid, fatty alcohol, cetyl alcohol, stearyl alcohol, non-penetrating steroid, free acid of steroid, lipid, ketorolac, silicone oil, olopatadine, prostaglandin, prostaglandin analog, prostamide, small-molecule integrin antagonist, lifitegrast, loteprednol, and fluoromethalone or a combination thereof.

The therapeutic active agent can include a prostaglandin analogue. The prostaglandin analogue can include at least one of bimatoprost, latanoprost, travoprost, and tafluprost. The therapeutic active agent can be for lowering the intraocular pressure of the eye. The therapeutic active agent can be for treating dry eye and/or related syndrome(s). In embodiments, the therapeutic active agent may include at least one of cyclosporine, steroid, loteprednol, fluoromethalone, non-penetrating steroid, free acid of steroid, non-steroidal anti-inflammatory, ketorolac, small-molecule integrin antagonist, lifitegrast, doxycycline, azithromycin, lipid, fatty alcohol, cetyl alcohol, stearyl alcohol, fatty acid, long chain fatty acid, oil, or silicone oil. The at least one therapeutic agent can include a steroid. The steroid may include at least one of loteprednol or fluoromethalone.

Table 1 shows examples of therapeutic agents suitable for use with the ocular devices described herein. The therapeutic agents can be used in many ways, and can include one or more of many therapeutic agents delivered.

TABLE 1

Non-limiting Examples of Indications and Therapeutic Agents

| Indication | Therapeutic Agent |
| --- | --- |
| Glaucoma | Prostaglandin or prostaglandin analog or prostamide (e.g. Bimatoprost, Travoprost, Latanoprost, or Tafluprost etc.) |
| Glaucoma | Prostaglandin or prostaglandin analog + second drug (e.g. latanoprost or bimatoprost) Bimatoprost + Carbonic Anhydrase Inhibitor (CAI) (dorzolamide) |
| Glaucoma (Canine and/or other veterinary) | Prostaglandin or prostaglandin analog or prostamide (e.g. Bimatoprost, Travoprost, Latanoprost, or Tafluprost) |
| Corneal Transplant, Prevention of Rejection | Steroid |
| Bacterial Conjunctivitis | One or more newer antibiotics that have little resistance built up |
| Dry Eye | Cyclosporine |
| | steroid (e.g. Loteprednol, Fluoromethalone) |
| | Non-penetrating steroid (e.g. free acid of steroid) |
| | Non-steroidal anti-inflammatories (e.g. Ketorolac) |
| | Small-molecule integrin antagonist (e.g. Lifitegrast) |
| | Doxycycline or azithromycin |
| | Non-pharmacologic agent (e.g. lipid) |
| | Fatty alcohol (e.g. cetyl alcohol or stearyl alcohol) |
| | Fatty acid (e.g. long chain fatty acid) |
| | Oil (e.g. silicone oil) |
| Post-Cataract Surgery | Antibiotic + Steroid; (NSAID optional) |
| Post-Laser Surgery | Antibiotic + Steroid; (NSAID optional) |
| Allergy | Olopatadine |
| | Antihistamine |
| | Steroid (e.g. Loteprednol, Fluoromethalone) |
| Trachoma | Doxycycline or other antibiotic |
| Blepharitis | Tetracycline, Doxycycline, Azithromycin, or other antibiotic |
| | Non-pharmacologic agent (e.g. lipid) |
| | Fatty alcohol (e.g. cetyl alcohol or stearyl alcohol) |
| | Fatty acid (e.g. long chain fatty acid) |
| | Oil (e.g. silicone oil) |

Although it is not intended to be a limitation of the invention, it is believed bimatoprost transports through the silicone matrix to its surface whereupon the agent becomes dispersed, dissolved or otherwise entrained with body fluid, e.g., tear liquid. The transport may be the result of and/or influenced by diffusion, molecular interaction, domain formation and transport, infusion of body fluid into the matrix or other mechanisms. For delivery to the eye, a therapeutically effective amount of bimatoprost transports to the exposed surface of the matrix whereupon tear liquid will sweep away the agent for delivery to target tissue or tissues.

EXAMPLES

Example 1: Stability of Bimatoprost with Acetonitrile (ACN) Wash

The purpose of this example was to evaluate the effect on stability (e.g., oxidative stability) of ocular inserts that have been washed with an organic solvent, acetonitrile.

The starting active agent, i.e., bimatoprost, was 99.9% pure. Bimatoprost, when degraded, primarily results in two degradation products, 5-trans and 15-keto. These degradation products were part of the impurities in a bimatoprost composition prepared by methods of the present disclosure. It was observed that in the method of preparing the ocular insert composition in which the formulation of bimatoprost was prepared—in part—by mixing bimatoprost with a polymer, the polymer containing bimatoprost was cured and thereby preparing the formulation, followed by molding, and washing with water, the level of 15-keto typically approached 0.3% of the total bimatoprost in the composition. However, after the composition was vacuum sealed in a foil pouch and e-beam sterilized, the level of 15-keto approaches 0.8%-0.9% of the total bimatoprost in the composition (Table 2). In contrast, an ocular insert composition made from the same formulation (i.e., as described above) that was molded, washed with acetonitrile, vacuum sealed in a foil pouch and e-beam sterilized, the degradation product of bimatoprost did not increase (Table 3).

TABLE 2

Assay and Percent Impurities for Water Washed, Pouched and Irradiated Product

| Sample | % Bimatoprost | % 5-Trans | % 15-Keto |
|---|---|---|---|
| 1 | 98.7 | 0.2 | 0.9 |
| 2 | 98.7 | 0.2 | 0.9 |
| 3 | 98.8 | 0.2 | 0.8 |
| 4 | 98.8 | 0.2 | 0.9 |
| 5 | 98.7 | 0.2 | 0.9 |
| 6 | 98.8 | 0.2 | 0.8 |
| 7 | 98.8 | 0.3 | 0.8 |

TABLE 3

Assay and Percent Impurities for ACN Washed, Pouched and Irradiated Product

| Sample | % Bimatoprost | % 5-Trans | % 15-Keto |
|---|---|---|---|
| 1 | 99.3 | 0.2 | 0.3 |
| 2 | 99.3 | 0.1 | 0.3 |

Therefore, washing the ocular inserts with acetonitrile prevented significant degradation (e.g., oxidative degradation) of bimatoprost during the e-beam sterilization process.

Example 2: Effect of Acetonitrile was on the Stability of an Ocular Insert Composition Active agent release rate testing of unwashed inserts was shown to have a high day 1 burst (>70 microgram/day) of active agent (initial release). This burst could be circumvented by washing the inserts prior to testing, which removed the outer layer of active agent. Wash conditions were optimized in order to achieve a burst of less than 60 µg of active agent on day 1 of release testing. The method in which the ocular inserts were washed with water provided the desired day 1 release rate, but the day-1 release rate increased after storage for greater than 1 month.

Long Term Release Rate with Acetonitrile Wash Process

Figure 2:
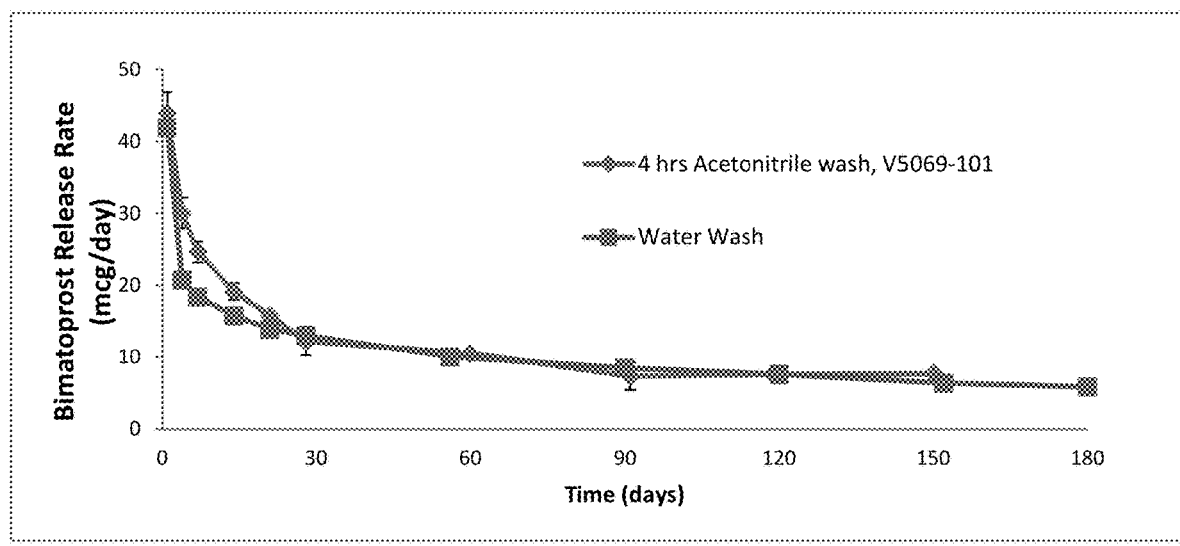
FIG. 2 shows line graphs of release rate of ocular inserts washed with acetonitrile and water.

The active agent release rate of acetonitrile-washed samples were compared against samples washed using the current water wash process. The release rate was comparable in the beginning for samples washed with acetonitrile but began to converge with the water-washed samples by day 28 (FIG. 2).

Increase in Day 1 Release Rate on Stability

The water-wash samples demonstrated an increase in day 1 active agent release upon storage at stability conditions (40° C./75% RH). The increase in day 1 release rate for these samples ranged between 20-40 µg/day.

Bimatoprost is a hygroscopic molecule and melts between 65-70° C. During the water wash process the solid state of the bimatoprost could change from crystalline to amorphous. In general, amorphous active agents are highly mobile and may diffuse to the surface of the silicone matrix faster due to the increased mobility. Washing the ocular inserts with a solvent other than water at ambient temperature could maintain the crystallinity of the active agent within the matrix and therefore the day 1 release rate would remain stable over time.

Figure 3:
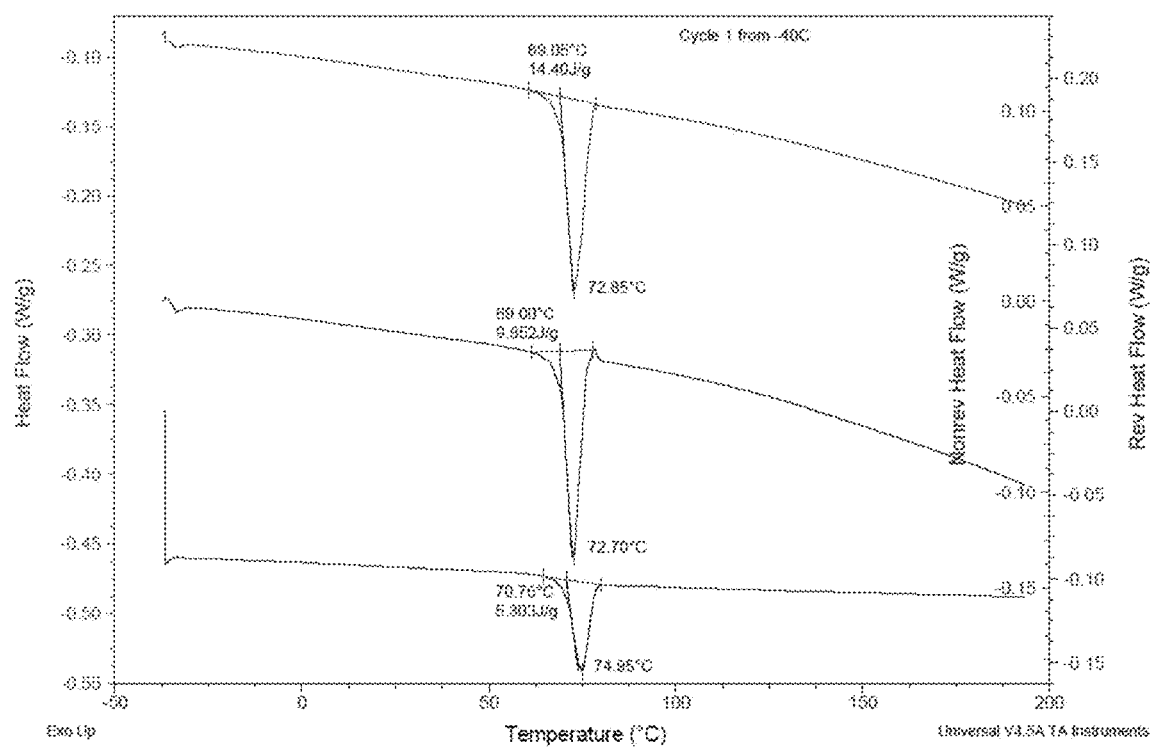
FIG. 3 shows MDSC scans for formulation washed with acetonitrile (ACN), showing cycle 1, heating from −40° C.
Figure 4:
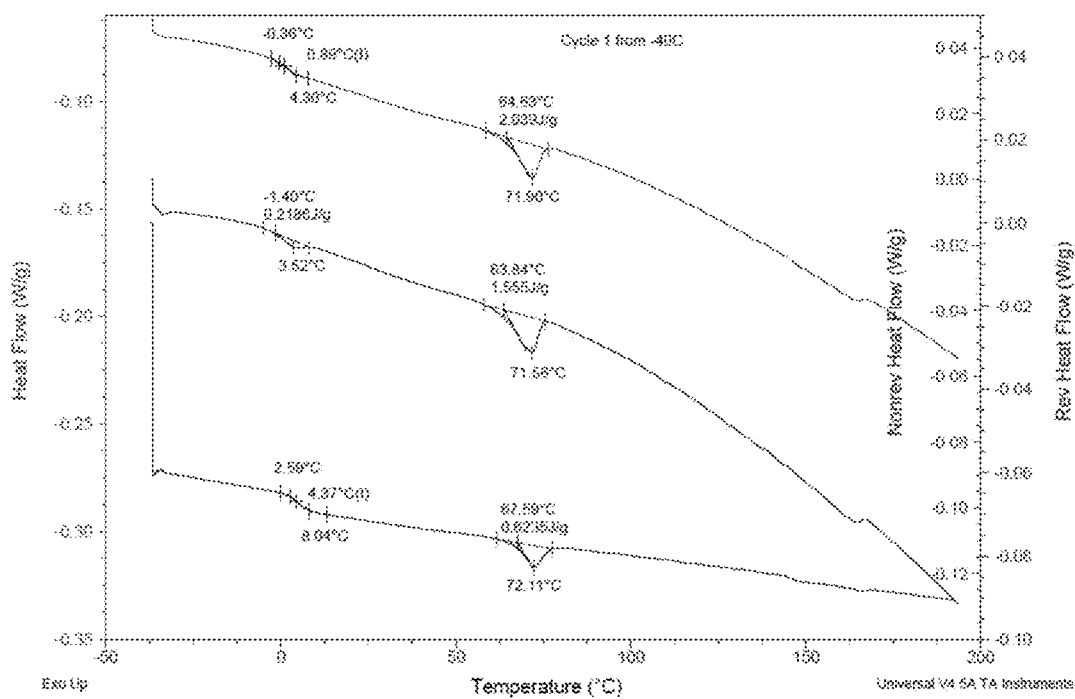
FIG. 4 shows MDSC scans for water wash formulation, 40 up mold, showing cycle 1, heating from −40° C.

To confirm, water and acetonitrile washed ocular inserts were tested with Modulated DSC (FIGS. 3 and 4). MDSC was run using a standard crimp sealed pan. The samples were cooled down to −40° C. at a rate of 30° C./min followed by an isothermal hold for 5 min and a ramp to 200° C. at a rate of 3° C./min with a ±1° C. modulation period every 60 s. The second cycle consisted of an isothermal hold for 1 min followed by cooling at 30° C./min to −80° C. then an isothermal hold for 5 min with a ramp of 3° C./min to 200° C. with a ±1° C. modulation period every 60 s.

The DSC analysis showed that inserts washed with acetonitrile (ACN) did not exhibit a Tg and had a melting point of 72° C. The DSC analysis showed that the active agent was mostly crystalline in the matrix. In contrast, in the ocular inserts washed with water the active agent was not mostly crystalline.

The water wash sample exhibited a Tg ranging from 4-6° C., and a melting point of 64.5° C. The non-reversing average enthalpy for the Tg of the water wash samples was 0.2402 J/g, which corresponded to an amorphous content of 13 w/w % (formulation basis) or 66 w/w % (active agent substance basis), based on the nominal active agent load of 20%.

Release rate testing was performed on the stability samples washed with ACN (Table 4). Based on the data gathered, day 1 active agent release appeared to be stable for samples washed with ACN.

TABLE 4

Day 1 Active Agent Release Result for ACN wash

| Storage Condition | Bimatoprost Day 1 Release (ACN Wash) | | |
|---|---|---|---|
| | T = 0 | T = 14 Days | T = 30 Days |
| RT | 35 | 40 | 36 |
| 40° C. | | 45 | 42 |

This study showed that washing of the ocular inserts with acetonitrile improved the stability of the product.

What is claimed is:

1. A method of producing an ocular insert for treating a disease or disorder of an eye of a subject, the method comprising:
   (i) mixing a therapeutic agent with a silicone polymer, thereby forming a silicone polymer matrix comprising the therapeutic agent, wherein the therapeutic agent is a prostamide, and wherein the silicone polymer comprises silica and poly(dimethylsiloxane-co-methylhydrosiloxane);
   (ii) curing the silicone polymer matrix into a cured silicone polymer matrix comprising the therapeutic agent; and
   (iii) washing the cured silicone polymer matrix with acetonitrile for 6 hours or less at a temperature 15° C. to about 20° C.; thereby removing the therapeutic agent from the outer layer of the cured silicone polymer matrix; thereby producing the ocular insert.

2. The method of claim 1, comprising washing the cured silicone polymer matrix with acetonitrile for 4 hours or less.

3. The method of claim 1, further comprising cooling the cured silicone polymer matrix prior to washing the cured silicone polymer matrix with acetonitrile.

4. The method of claim 1, wherein step (i) comprises dissolving the therapeutic agent in an organic solvent to form a solution; mixing the solution with the silicone polymer, thereby forming the silicone polymer matrix comprising the therapeutic agent; and removing the organic solvent before curing the silicone polymer matrix.

5. The method of claim 1, further comprising sterilizing the cured silicone polymer matrix.

6. The method of claim 1, further comprising forming the cured silicone polymer matrix into a ring shape.

7. The method of claim 1, wherein the silicone polymer comprises a first component comprising silica and a second component comprising silica and poly(dimethylsiloxane-co-methylhydrosiloxane), wherein the ratio of the first component to the second component is 1:1.

8. The method of claim 1, wherein the prostamide is bimatoprost.

9. The method of claim 1, wherein the therapeutic agent is in a crystalline form or a semi-crystalline form.

10. The method of claim 1, wherein the temperature in step (iii) is about 20° C.

* * * * *